United States Patent [19]
Hanna

[11] Patent Number: 5,568,263
[45] Date of Patent: *Oct. 22, 1996

[54] NON-CONTACT INSPECTION SYSTEM

[75] Inventor: James L. Hanna, Ann Arbor, Mich.

[73] Assignee: Mectron Engineering Company, Ann Arbor, Mich.

[ * ] Notice: The term of this patent shall not extend beyond the expiration date of Pat. No. 5,383,021.

[21] Appl. No.: 369,360

[22] Filed: Jan. 6, 1995

Related U.S. Application Data

[63] Continuation-in-part of Ser. No. 49,172, Apr. 19, 1993, Pat. No. 5,383,021 Jan. 17, 1995.

[51] Int. Cl.⁶ .................................................. G01B 11/04
[52] U.S. Cl. ........................................ 356/385; 356/394
[58] Field of Search .................................. 356/376, 383, 356/384, 385, 386, 387, 394; 250/559.12, 559.13, 559.15, 559.19, 559.22, 559.26

[56] References Cited

U.S. PATENT DOCUMENTS

| | | |
|---|---|---|
| 2,812,685 | 11/1957 | Vossberg . |
| 3,604,940 | 9/1971 | Matthews ........................ 356/386 |
| 3,724,958 | 4/1973 | Callan . |
| 3,727,067 | 4/1973 | Shepherd ........................ 356/383 |
| 3,749,500 | 7/1973 | Carlson et al. ................. 250/559.15 |
| 4,021,119 | 5/1977 | Stauffer ........................ 356/386 |
| 4,031,368 | 6/1977 | Colding et al. ................. 356/384 |
| 4,061,427 | 12/1977 | Fletcher et al. ................ 356/384 |
| 4,067,652 | 1/1978 | Bohlander . |
| 4,115,702 | 9/1978 | Nopper ............................ 356/384 |
| 4,122,525 | 10/1978 | Eaton . |
| 4,171,161 | 10/1979 | Jung ................................ 356/383 |
| 4,260,260 | 4/1981 | Letort et al. .................... 356/385 |
| 4,395,119 | 7/1983 | Nakata et al. . |
| 4,417,147 | 11/1983 | Faville .......................... 356/376 |
| 4,476,533 | 10/1984 | Daudt et al. . |
| 4,532,723 | 8/1985 | Kellie et al. .................. 356/385 |
| 4,576,482 | 3/1986 | Pryor . |
| 4,676,648 | 6/1987 | Schulz et al. . |
| 4,875,777 | 10/1989 | Harding . |
| 4,880,991 | 11/1989 | Boehnlein et al. . |
| 4,914,307 | 4/1990 | Kanev ............................ 356/387 |
| 4,978,223 | 12/1990 | Kutchenriter et al. . |
| 4,991,308 | 2/1991 | Donaldson . |
| 5,164,995 | 11/1992 | Brooks et al. .................. 356/383 |
| 5,383,021 | 1/1995 | Hanna ............................ 356/383 |

FOREIGN PATENT DOCUMENTS

| | | | |
|---|---|---|---|
| 1590632 | 5/1970 | France ........................... | 356/385 |
| 3633275 | 10/1987 | Germany . | |

*Primary Examiner*—Richard A. Rosenberger
*Attorney, Agent, or Firm*—Harness, Dickey & Pierce, PLC

[57] ABSTRACT

An improved non-contact inspection system capable of evaluating spatial form parameters of a workpiece to provide 100% inspection of parts in production. The system causes parts to be sequentially loaded onto an incline track where they pass through a test section. The test section includes a length detection array for measuring the length of the workpiece, which includes a source generating a sheet of light oriented in the longitudinal direction of the workpiece. The profile of the parts are evaluated by one or more light sources also creating a sheet of light oriented transverse to the longitudinal axis of the parts. First and second pairs of single channel photodetectors are provided for each of the light sources which provides a pair of analog outputs of the extent to which each sheet of light is occluded by the part, as well as an ability to eliminate noise or scintillation caused by a point source of light, for example with a laser light source. These outputs are analyzed through appropriate signal processing hardware and software to generate length and profile data related to the workpiece geometry.

18 Claims, 6 Drawing Sheets

NON-CONTACT INSPECTION SYSTEM

CROSS REFERENCE TO RELATED APPLICATION

This is a continuation-in-part of U.S. patent application Ser. No. 08/049,172 filed on Apr. 19, 1993, and issued as U.S. Pat. No. 5,383,021, on Jan. 17, 1995.

BACKGROUND AND SUMMARY OF THE INVENTION

This invention relates to a device for inspecting components and particularly to one using an array of light sources and photodetectors as a means of evaluating a component for conformance to spatial form criteria.

Presently, there is an ever increasing demand to obtain high quality products which has resulted in a significant increase in the use of non-contact inspection systems. In order for a complex machine to operate as designed, it is necessary that all of its sub-components comply with quality criteria. In some manufacturing settings, customers require 100% inspection of component parts. For example, fasteners used in the automobile industry and elsewhere often must be individually inspected to determine if they meet spatial form and other criteria.

Numerous types of inspection systems are presently utilized. One type of system uses contact probes which touch a component at various points to determine if its dimension or profile meet certain criteria. However, contact devices have inherent limitations in that they are subject to wear and generally require that the component and the contact probe be accurately positioned during the evaluation process. Moreover, such devices are generally slow to operate and are limited in terms of the number of criteria and complexity of profiles which they can evaluate.

A variety of non-contact systems are also known using a variety of techniques. For example, ultrasonic inspection systems examine reflected sound waves as a means of characterizing a component. Various systems based on a video image of a part are also known. In addition, laser gauging systems are used in which specific dimensional measurements can be obtained.

However, although known non-contact inspection systems are generally extremely useful, they have certain limitations. Many of the presently available non-contact gauging systems require complex data processing approaches which impose expensive hardware requirements and can limit the speed with which evaluations can be accomplished. Preferably, evaluation of a workpiece can be conducted in a rapid enough fashion that the parts can be directly sorted into qualified or disqualified part streams. Many of these prior art systems also tend not to be easily adapted to various part configurations or for evaluating different features of a part. Moreover, many of the currently available non-contact inspection systems have limitations in terms of the number of parameters which can be effectively examined during the inspection process. Another disadvantage of some known systems is their limitations in terms of the types of parameters which can be considered. For example, often fine details of thread profiles of fasteners are needed. Moreover, many prior art systems, although performing adequately in a laboratory setting, are not sufficiently rugged for a production environment where temperature variations, dust, dirt, cutting fluids, etc. are encountered.

In accordance with this invention, an improved non-contact inspection system is provided which enables rapid inspection to be conducted permitting parts to be immediately sorted in terms of being in conformance or out of conformance with spatial form criteria. Moreover, a hard copy of part geometry can be generated pointing out specific form discrepancies. For example, for a threaded fastener, the diameter, length, profile and threads can be evaluated. When producing fasteners, the process often begins with wire stock which is fed into a cold heading or screw type forming machine. The part is die-formed or cut in a machine into a shape that may include several diameters and possibly a threaded or knurled length. The formed part may require secondary operations such as thread rolling, heat treating, plating etc. It is not uncommon for one or more of the processes to fail to produce the desired geometry of part. The occurrence of such defects is often not adequately monitored through random part selection or other quality assurance processes which do not provide 100% inspection. The inspection system of this invention is also highly adaptable for evaluating various components.

In applicant's co-pending U.S. patent application Ser. No. 08/049,172 an inspection system is provided wherein parts move by gravity or other means along a track through a test section. Initially, the part length is established through the use of a length detection array having a number of light sources and associated photodetectors. One of the sources generates a sheet of light oriented in the direction of travel of the part. The extent to which the sheet of light is blocked by the part is related to its length. In addition, the part passes through a profile detection array having one or more of light sources whose output is also in the configuration of a sheet of laser light oriented perpendicular to the part motion which cuts through the part as it moves past. Significantly, the evaluation of component length and profile in accordance with this invention is achieved through the use of single channel photodetectors. The use of single channel output photodetectors in accordance with this invention inherently provides advantages in terms of signal processing and data reduction.

In accordance with this invention, an improved non-contact inspection system is provided which enables rapid inspection of parts, yet enhances detection of certain profile features which under certain conditions might pass undetected through Applicant's co-pending inspection system. Namely, a profile detection array employs two linear detectors oriented along a line which are positioned such that their junction is positioned that are in contact at approximately the center line of a part to be inspected which are used in place of a single detector as disclosed in Applicant's co-pending system. The improved profile detection array has one or more light sources whose output is in a sheet of laser light oriented perpendicular to the part motion which cuts through the part as it moves past. Each photo detector output will produce an analog signal proportional to the profile of one half of the part (i.e. above or below the part center line). As a result, thread profiles will be displayed which might otherwise be missed by a single detector array, since some geometries, such as threads viewed from a certain pitch and/or angle of the sheet of light, would otherwise occlude the same amount of light.

Preferably, a laser diode is mounted in a housing where it passes first through a lens and then through an achromat lens to produce a sheet of light. Subsequently, the sheet of light passes through a 50/50 beam splitter.

One half of the light which passes through the beam splitter impinges on a first pair of photovoltaic cells, namely the pair which display the part occlusion, wherein a part to be detected passes through the beam of light to partially occlude the first pair of detectors. The other half of light which reflects from the beam splitter impinges on a second pair of photovoltaic cells. With this arrangement, noise or scintillation of the laser signal can be digitally filtered since the same noise is present on both pairs of photodetectors. Namely, the laser which is a spot source produces a uniform noise across the sheet of light between the sender and receiver. By subtracting spurious output differences between the two pairs of photodetectors, any noise can be filtered out.

The profile detection array of this invention utilizes a plurality of elements forming the arrays arranged in a radial physical arrangement similar to Applicant's co-pending application. However, the laser element in each array, or element is turned on or modulated in a circular pattern. By modulating the pattern of elements in an alternating radial arrangement, any receiver interaction is eliminated which might be caused by stray reflections from the part being inspected inadvertently by another element.

Additional benefits and advantages of the present invention will become apparent to those skilled in the art to which this invention relates from the subsequent description of the preferred embodiments and the appended claims, taken in conjunction with the accompanying drawings.

DETAILED DESCRIPTION OF THE PREFERRED EMBODIMENT

Figure 1:
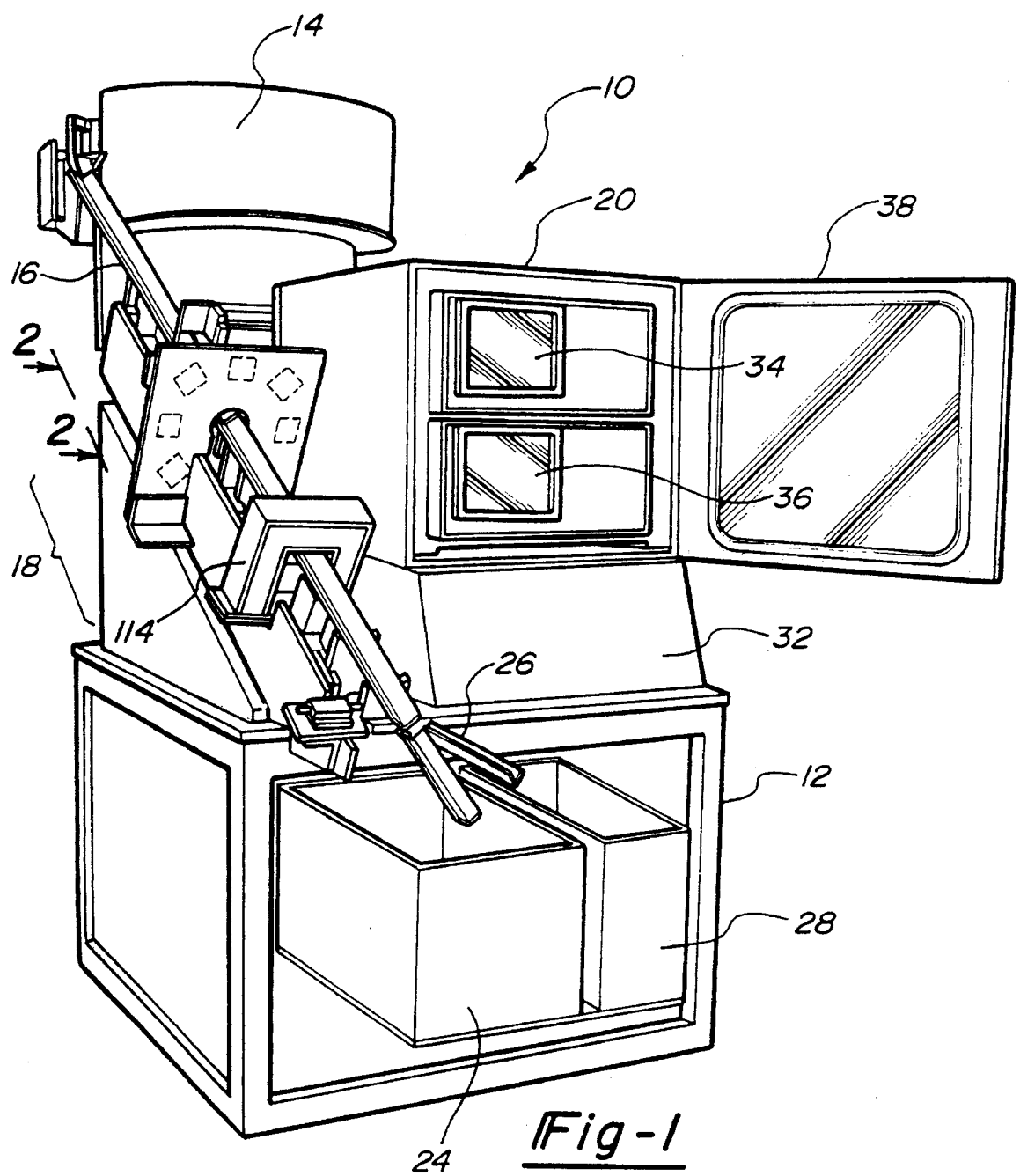
FIG. 1 is a pictorial view of the non-contact inspection system according to this invention.

A non-contact inspection system in accordance with this invention is shown in FIG. 1 and is generally designated there by reference No. 10. Inspection system 10 was disclosed in Applicant's co-pending U.S. patent application Ser. No. 08/049,172 which is hereinafter incorporated by reference. System 10 is hereinafter described in conjunction with improved profile detection features wherein light sources 68, 70, 72 and 74, as well as photodetector 76, 78, 80 and 82 from Applicant's co-pending application are replaced with improved corresponding devices. Inspection system 10 generally comprises frame 12, part sorter 14, slide track 16 having test section 18, and enclosure 20 for housing electronic components of the instrument.

Figure 6:
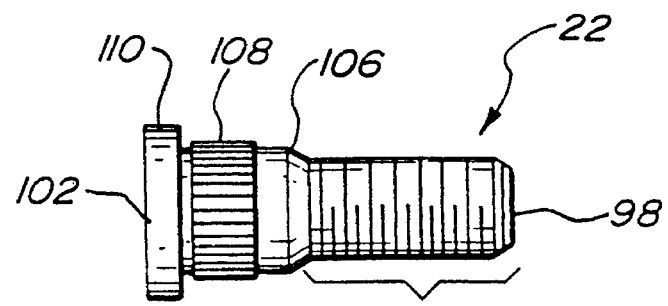
FIG. 6 is an elevational view of a representative workpiece for evaluation.

While inspection system 10 can be used for numerous types of workpieces, an example of one such component is provided in FIG. 6 in the form of a threaded bolt 22 used for mounting the road wheels of a motor vehicle. A large number of bolts 22 (referred to also as "parts" or "workpieces") are dumped into part sorter bin 14. Part sorter 14 causes the randomly oriented bolts 22 to be directed in a desired orientation i.e. headed or threaded end first, and causes them to periodically slide down track 16 under the force of gravity. As parts 22 pass through test section 18, they are evaluated as will be described in more detail in the following portions of this specification. Bolt 22 is inspected for conformance with predetermined spatial form criteria. If a particular part meets the criteria, it passes into parts bin 24 provided for qualified or "good" parts. If, however, the part is deemed to be out of conformance, gate 26 is actuated and the part is diverted into parts bin 28 provided for disqualified or "bad" parts. Presumably, good parts will outnumber bad parts and the parts bins are sized accordingly.

Within enclosure 20 is housed computer 32 provided for evaluating the outputs of the system, controlling the system, and providing a means of storing data related to part criteria and inspection history. A pair of displays 34 and 36 is provided, one of which may output in graphical form configuration data for a particular part, whereas the other may be used for outputting statistical or other numerical data related to inspection. In a prototype embodiment of this invention, displays 34 and 36 were electroluminescent types having touch screens for interaction with the user. Enclosure 20 has access door 38 which can be closed when the system is not in use.

Details of the elements and operation of test section 18 will be described with reference to FIGS. 2 and 3. Within test section 18, two distinct evaluations of part 22 are provided. The length of the part (i.e., its dimensions along its direction of travel) is evaluated using length detection array 40, whereas its radial profile (i.e., its form perpendicular to its direction of travel) is evaluated by profile detector array 166.

Length detection array 40 includes length measuring detector 42, and a number of spot laser detectors 44, 46, 48, 50, 52, 54 and 56. Length measuring detector 42 includes a light source 43 which is preferably a semiconductor laser emitting (for convenience) visible light, and photodetector 45. Internally within light source 43 are cylindrical lens elements which spread the beam to define a sheet of light 60 designated by the parallel lines shown in FIG. 2. One laser detector found acceptable for use in conjunction with the present invention is manufactured by the Keyence Company and is designated as model series LX2. Light source 43 provides a sheet of light 60 having a 1 mm thickness (measured perpendicular to the part motion shown by the arrow) and a 30 mm length (measured parallel to the part motion). Since sheet of light 60 is comprised of parallel rays, when a portion of the sheet of light is occluded by part 22, a shadow is created which does not appreciably vary in dimension with distance from the part. Photodetector 45 includes an internal focusing lens and an internal photodiode. As shown in FIG. 2, light source 43 and photodetector 45 are positioned with slide track 16 therebetween. Part 22 interrupts the transmission of light to photodetector 45. A slide track slit 61 allows light to pass through the track when a part is not passing through test section 18.

In operation of length detector array 40, when no portion of sheet of light 48 is occluded, the entire output of laser source 43 is received by photodetector 45 and an electrical output signal is provided based on the uninterrupted light striking the photodetector. However, when any portion of sheet of light 60 is occluded, a corresponding reduction in electrical output from photodetector 45 results. Accordingly, photodetector 45 provides an analog output which is a function of the percent of sheet of light 60 which is blocked and therefore not incident upon the photodetector, which is a measure of the length of the part. Although the thickness of sheet of light 60 is not critical, it is narrower than part 22 so that the sheet of light will be occluded as it passes through test section 18.

If parts 22 having a length which is less than the length of sheet of light 60 (i.e. 30 mm is one example) are to be evaluated, no further detectors would be necessary for measuring the length of workpieces beyond length measuring detector 42. This is the case since when such a part is within the confines of sheet of light 60, the proportion of the light which is not occluded is a length measure. However, a longer part fully occludes sheet of light 60 so that the only information provided is that the part length exceeds the length of the sheet of light. However, inspection system 10 is designed to be used with workpiece lengths which exceed that of the length of sheet of light 60. Accordingly, individual length spot detectors 44 through 56 are provided. Each of these devices includes an internal semi-conductor laser source which creates a concentrated beam which is incident upon a surface of V-shaped slide track 16. Length spot detectors 44 through 56 further integrally include a photodetector. These devices are mounted such that when no workpieces are present along slide track 16, the internal photodetector receives a reflected signal from its associated source. The devices are positioned such that when a part 22 slides past them, the reflected light is interrupted by scattering or reflection, thus enabling the presence of the workpiece at that spot to be determined through a reduced photodetector output.

Figure 2:
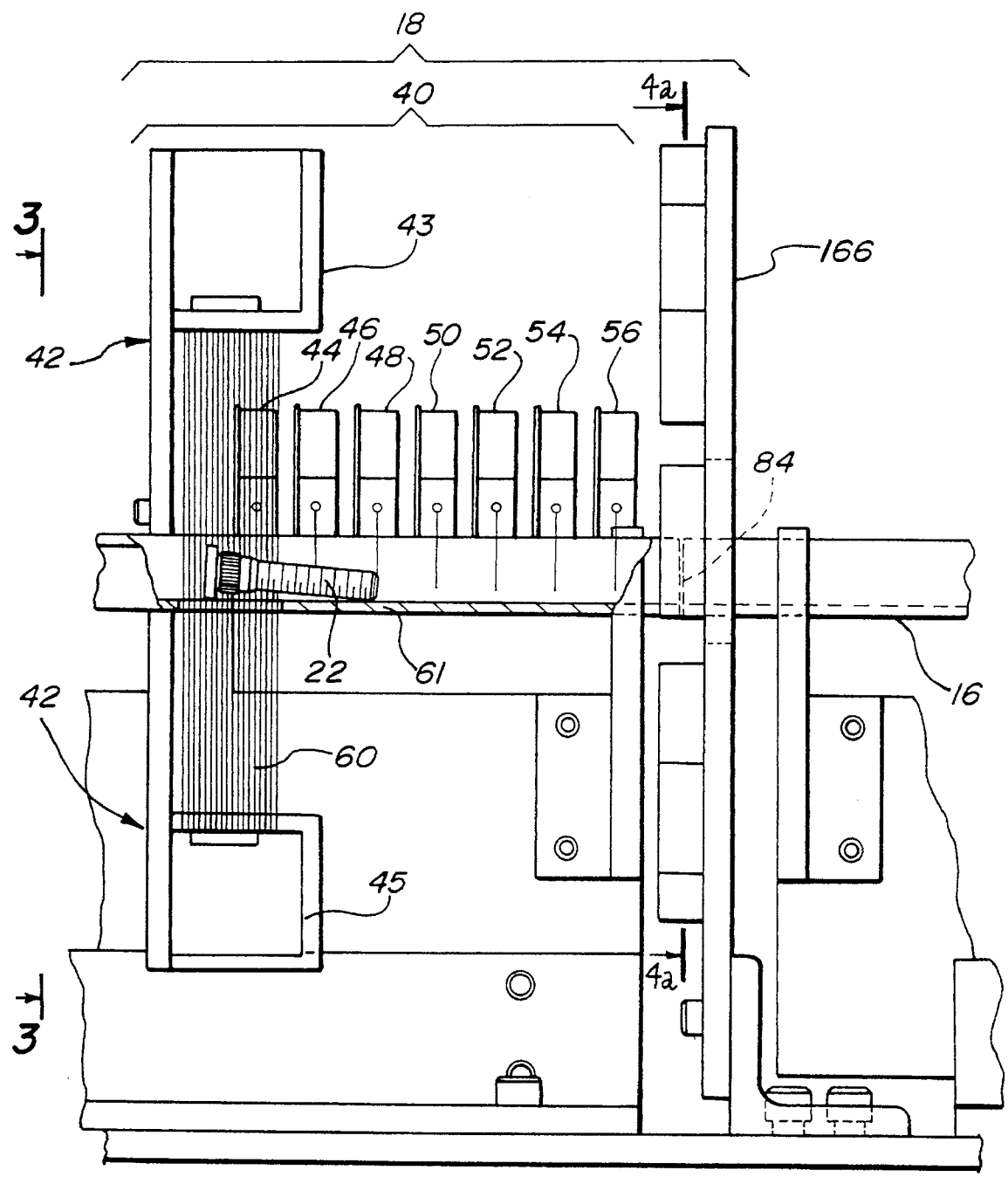
FIG. 2 is a view taken along line 2—2 of FIG. 1 particularly showing the test section and its length detection array.

FIG. 2 shows length spot detectors 44 through 56 located at regular intervals along slide track 16 downstream of length measuring detector 42. Conveniently, length spot detectors 44 through 56 are positioned at one inch intervals or some other regular index location. In operation, when the output of photodetector 45 indicates complete occlusion of sheet of light 60, it is known that the full length of the workpiece 22 cannot be determined solely by the output of photodetector 62. The output of photodetector 62 is evaluated at the instant that each of length spot detectors 44 through 56 first senses the position of the workpiece. In the example shown, this array of spot detectors allows parts having lengths up to 7 inches to be evaluated. As shown in FIG. 2, workpiece 22 is shown at a position as it slides through test section 18 at the threshold of detection by length spot detector 46. Since at this point sheet of light 60 is not completely occluded, it is known that a part length measurement can be made. In this example, the total length of the part is known to be 2 inches added to the length which is measured by the percent of sheet of light 60 being occluded as measured by photodetector 45.

In addition to providing an accurate measure of the length of part 22, length detection array 40 further enables the velocity of the part to be detected if the length of the part is known in advance or can be calculated through evaluation of profile information. As will be described in more detail below, this measure of velocity is important since inspection system 10 does not need the velocity of the part to be accurately controlled through test section 18. Control over workpiece velocity is not needed, allowing use of a simple inclined track by which the parts are directed through test section 18. Moreover, the system's lack of need for accurate velocity control of the part is a distinct advantage since such a requirement would likely add cost and complexity to the system.

Figure 3:
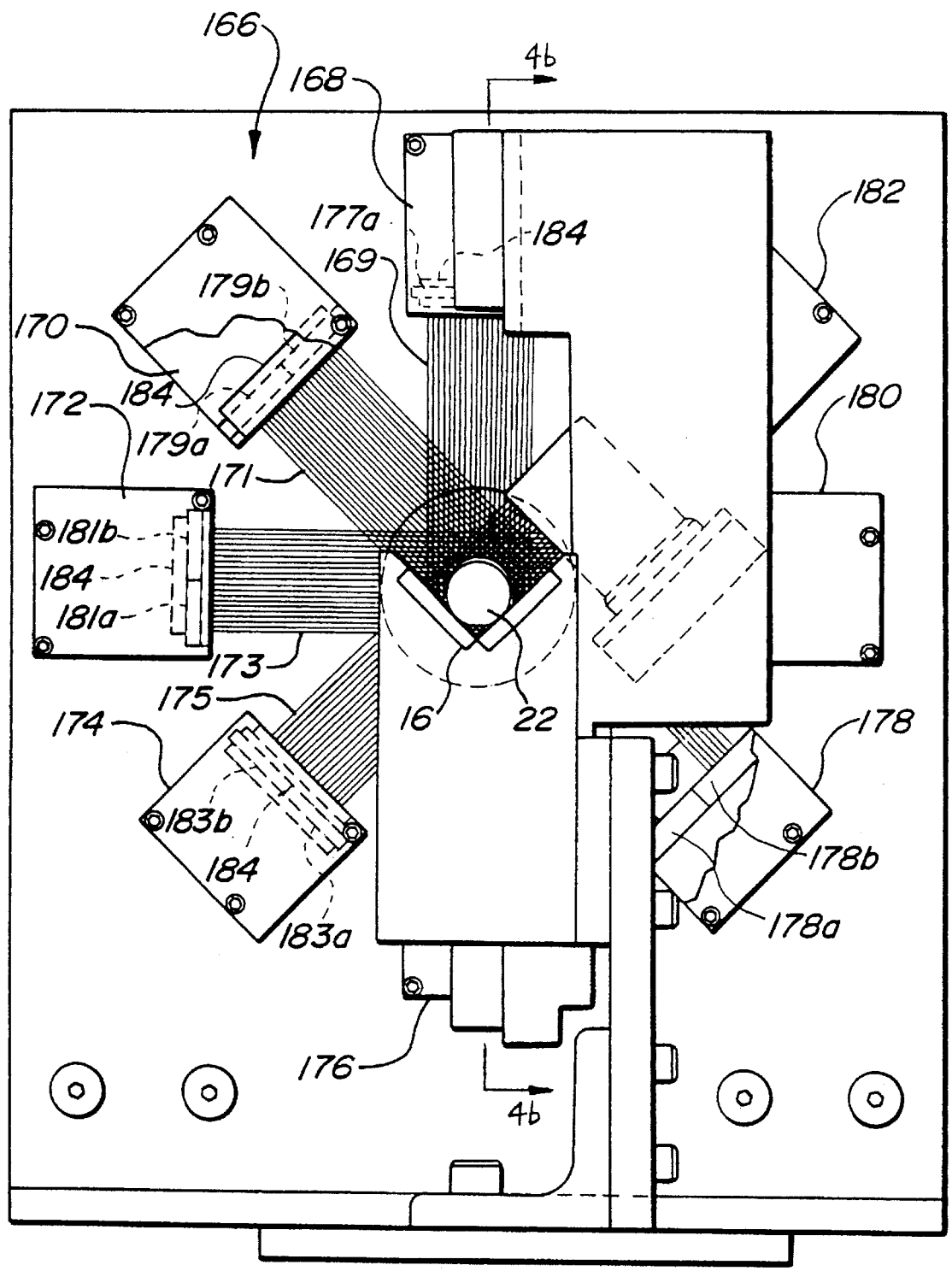
FIG. 3 is a view taken along line 3—3 of FIG. 2 particularly showing the radial detection array of the test section of the instrument in accordance with this invention.

Now with reference to FIG. 3, a profile detection array 166 is shown in detail. Profile detection array 166 substitutes generally for array 66 in Applicant's co-pending application. Profile detection array 166 includes a series of four detectors, having light sources 168, 170, 172, and 174, each with corresponding first and second pairs of photodetectors 176a, 176b and 177a, 177b; 178a, 178b and 179a, 179b; 180a, 180b and 181a, 181b; 182a, 182b and 183a, 183b, respectively. Each of the light sources 168 through 174 are identical to laser light source 43 described previously. Similarly, photodetectors 176 through 183 are identical to photodetector 45 described previously. However, instead of using a single photodetector a first pair of photodetectors are positioned side-by-side to detect workpiece-occluded light and a second pair of photodetectors are positioned side-by-side to detect non-occluded light from the same light source wherein the non-occluded light is used to cancel out any noise introduced by the light source. Accordingly, each of the light sources 168 through 174 generate a sheet of light 169, 171, 173, and 175, respectively, having the characteristics previously described.

Figure 4A:
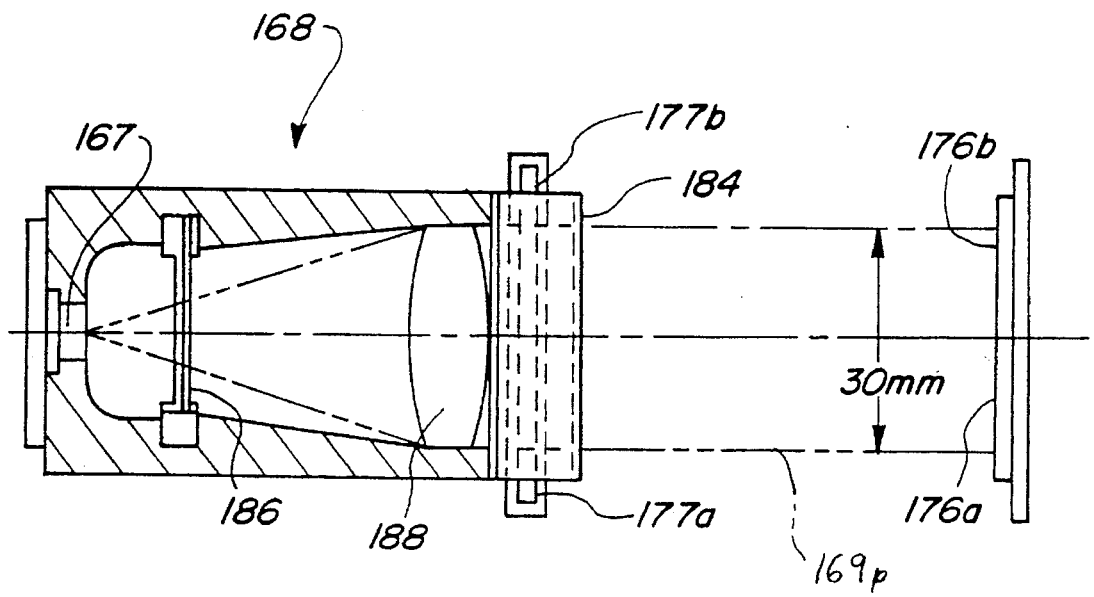
FIG. 4a is a centerline sectional view taken along line 4a–4a of FIG. 3 particularly showing one of the light sources and the pairs of photodetectors of the profile detection array of this invention.
Figure 4B:
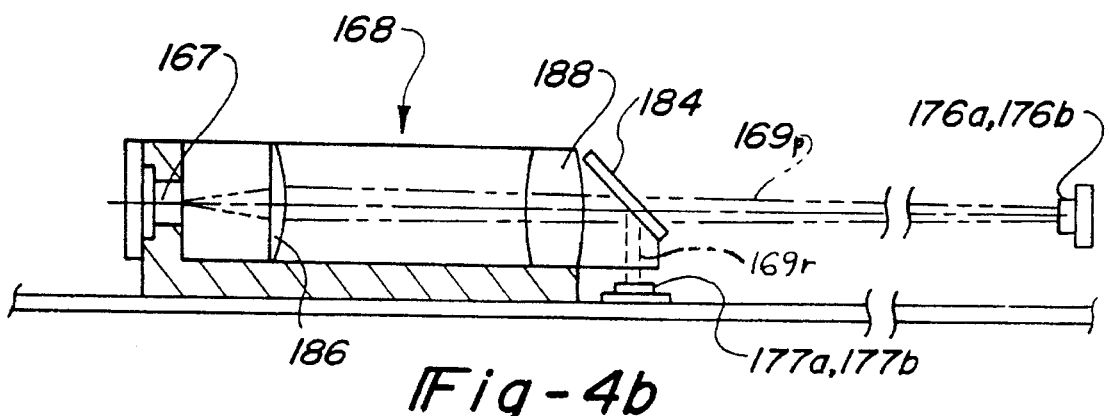
FIG. 4b is a partial centerline sectional view taken along line 4b–4b of FIG. 3 particularly showing one of the light sources and the pairs of photodetectors of the profile detection array of this invention.

FIGS. 4a and 4b depict construction of one of the light sources 168 along with an accompanying first pair of photodetectors 176a, 176b for detecting part occluded light and a second pair of photodetectors 177a, 177b for detecting non-occluded light. Likewise, light sources 170–174 operate in conjunction with corresponding first pairs of photodetectors 178a, 178b; 180a, 180b; 182a, 182b, respectively, and second pairs of photodetectors 179a, 179b; 181a, 181b; and 183a, 183b, respectively. Preferably, light source 168 is constructed from a laser diode 167 mounted in a housing 190 containing a cylindrical lens 186 and an achromat lens 188 which cooperate to produce a beam of light that has a divergence of 8° vertical and 31° horizontal. The beam of light passes through the cylindrical lens and the achromat lens to effect a collimated sheet of light approximately 30 mm wide and 1 mm or less in thickness. Furthermore, the sheet of light 169 then passes through a 50/50 beam splitter 184.

A first portion of the light 169p from the sheet of light 169, preferably one half of the light passes through the beam splitter and impinges directly on the first pair of photodetectors 176a, 176b, or photovoltaic cells. A machine part is furthermore detected as it passes through sheet of light 169p. The remaining portion of light 169r from the sheet of light 169 is reflected by beam splitter 184 and impinges directly on the second pair of photodetectors 177a, 177b which are substantially the same as the first pair of photodetectors that detect the part occlusion.

The second pair of photodetectors allow for detection of laser signal noise or scintillation, which can then be subtracted from the signal derived from the first pair of photodetectors, substantially filtering the signal digitally. The light source 168, or laser is essentially a spot source which produces a uniform noise across the sheet of light at both the sender and receiver. Therefore, any noise present can be filtered by subtraction of the spurious voltage difference between the actual signal produced by occlusion in the complete signal as detected by the second pairs of photodetectors.

Similar to photodetector 45, photodetectors 176–183 also integrate the received output of the corresponding light source and provide an analog output related to essentially one half of the associated sheet of light directed at each respective detector. By combining the detected light from pairs of adjacent photodetectors, the complete sheet of light can be monitored. For example, by monitoring a first pair of photodetectors 176a, 176b as a machine part passes through the accompanying sheet of light 169p, a pair of analog outputs are produced which are related to the percent of occlusion of the associated sheet of light. By furthermore monitoring the second pair of photodetectors 177a, 177b and subtracting respective analog output signals from the corresponding output signals from photodetectors 176a, 176b, noise is removed from the signal and the corresponding analog output signals more clearly relate to the percent of occlusion of the associated sheet of light 169.

In order to permit transmission of the sheets of light 169–175, slide track 16 features a through slit 84 shown in FIG. 2. Sheets of light 169–175 are oriented such that the cross-sections of the part are fully within the width of the sheet of light so that the full extent of the cross-section can be evaluated. Preferably, each sheet of light is aligned to substantially center with respect to the centerline, or major axis of a part being detected. In the configuration shown, the workpiece 22 has a maximum cross-section thickness which is less than the length of sheets of light 169–175. If thicker parts are to be evaluated, additional spot detection could be used as described in connection with the length detector array 40, or the pair of photodetectors can be spaced apart at locations which assure detection of the outer edges of the part so as to partially light occlude each detector as a part passes by.

If the workpiece 22 is entirely rotationally symmetric, and lacks any presence of threads or fine features which might vary circumferentially, only a single light source 168 with a single first pair of photodetectors 176a, 176b and a second pair of photodetectors 177a, 177b of profiled detector array 166 would be needed. However, many workpieces with which inspection system 10 would be used can be expected to have asymmetrical configurations such as flats cut along one portion, threads along their surface, etc. In order to maximize the ability of inspection system 10 to evaluate such various configuration features, the four light, or laser sources 168–174 and associated photodetectors 176–183 are provided at 45° angular positions relative to adjacent detectors, namely the display positions as shown in FIG. 3.

Figure 5:
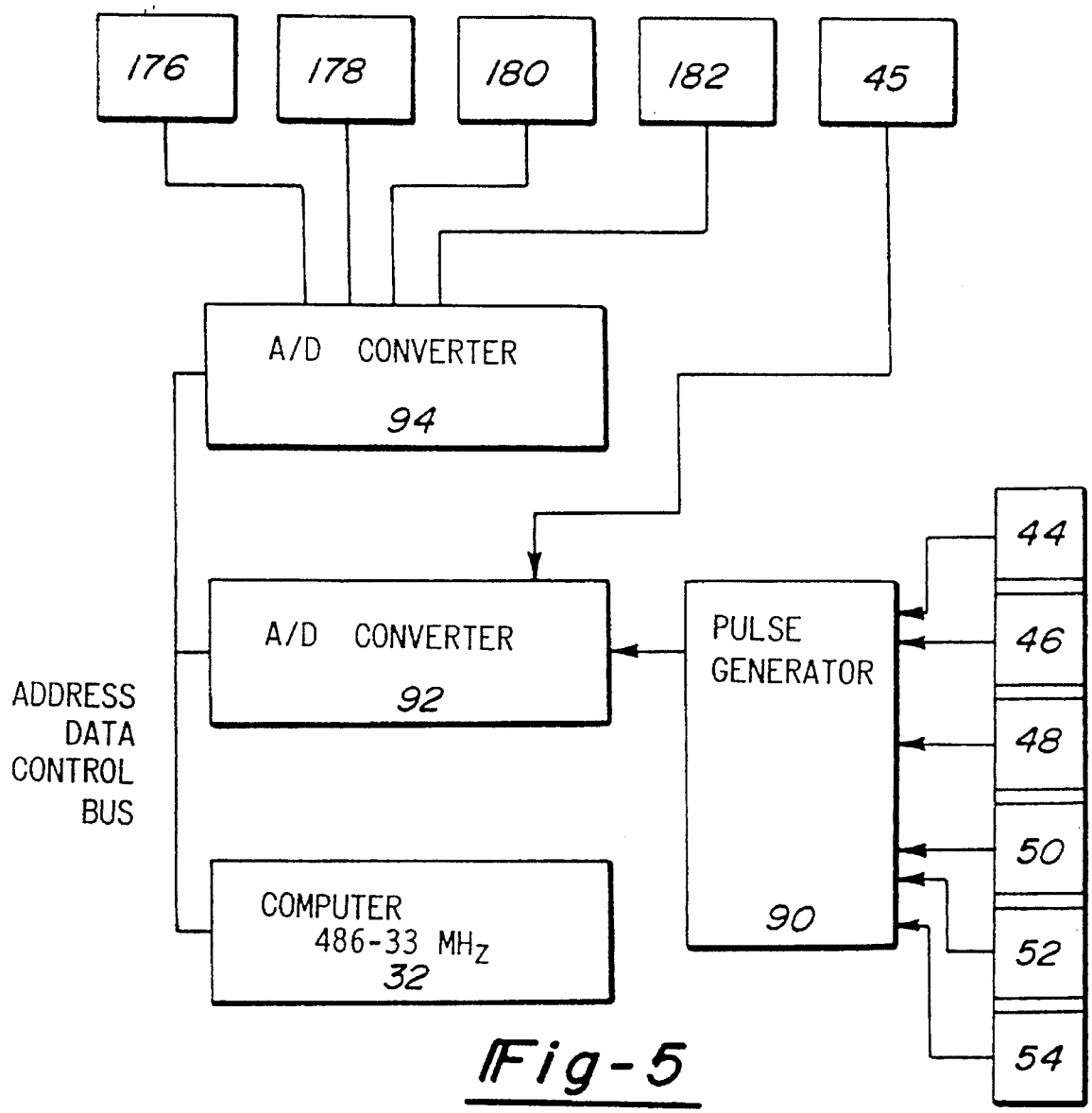
FIG. 5 is a schematic diagram of the photodetectors, light sources and signal processing and control system of the inspection system of this invention.

FIG. 5 provides a schematic diagram of the electronic signal processor and controller 88 of the device of this invention. In an experimental embodiment of the invention an Intel 486 processor based multi-purpose computer 32 is provided to perform many of the functions of processor and controller 88. The length measuring photodetector 45 along with the various spot lasers 44–56 fed through pulse generator 90 for shaping their output are fed to analog-to-digital (A to D) converter 92. Converter 92 is externally triggered, for example through the use of a gate or light interrupter which detects parts loaded onto slide rack 16. Profile measuring photodetectors 176a, 176b through 183a, 183b provide signals through A to D converter 94, all of which are processed and displayed through computer 32 in associated displays. Each group of first pairs of photodetectors and second pairs of photodetectors, for example photodetectors 176a, 176b and photodetectors 177a, 177b are sampled discretely such that each of the four groups of four detectors are sampled alternatively by turning on laser elements 168–174 in an alternating, or modulated manner in a circular pattern. By alternately radially turning on light sources and respective detectors, receiver interaction is eliminated which might produce stray reflections off the part which are inspected by non-accompanying photodetectors, for example, photodetectors 176a, 176b and 177a, 177b should only detect light from light source 168. Therefore, light source 168 is turned on in conjunction with photodetectors 176a, 176b and 177a, 177b. Subsequently, the next light source 170 is turned on briefly along with accompanying photodetectors 178a, 178b and 179, etc. Software resident in the computer 32 controls the sequential alternating activation of the light source and accompanying photodetectors in each array. Furthermore output from corresponding first and second pairs of photodetectors are subtracted, digitally, in order to eliminate noise from each respective reading. A to D converter 94 is gated under software control based on the output of A to D converter 92.

Figure 7:
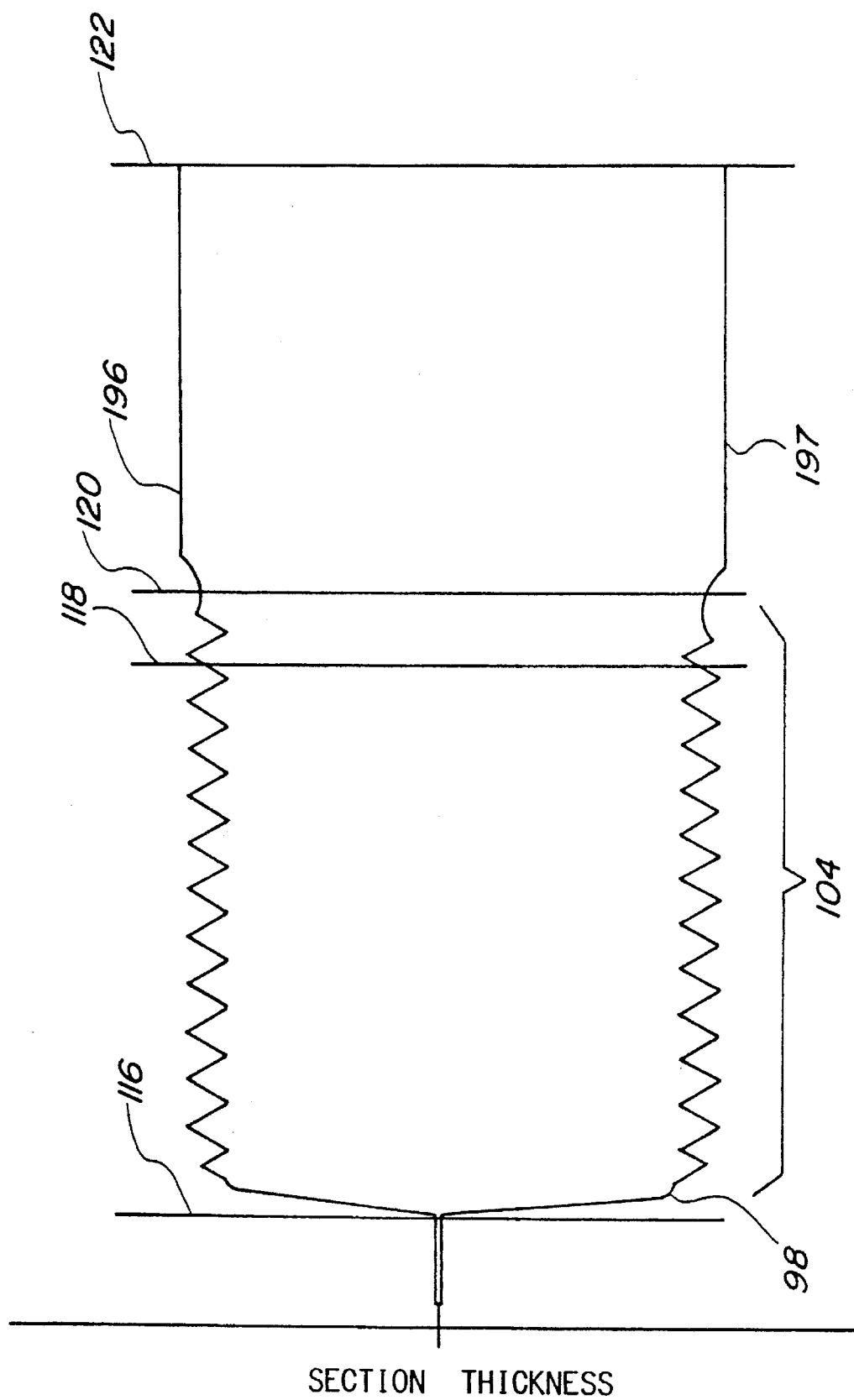
FIG. 7 is a representative output showing a partial component profile configuration provided by the instrument of the present invention and evaluating the threaded end of the workpiece shown in FIG. 6.

FIG. 7 shows an example profile of the output of laser inspection system 10 generated from an inspection of the threaded end of bolt 22 shown in FIG. 6. Although curves 196 and 197 together resemble a true profile of the part, it is instead the analog output of a large number of digitally sampled discrete analog outputs from a first pair of photodetectors, for example photodetectors 176a, 176b minus the analog outputs of the corresponding second pair of photodetectors, for example photodetectors 177a, 177b plotted with respect to time or length of workpiece 22. In otherwords, curves 196 and 197 are both plots of substantially one half of the section thickness of part 22 along its detected length. Furthermore, each adjacent plotted analog output are separated by the time required to also collect samples for the other three remaining pairs of photodetectors. The profile of curve 196 and 197, however, clearly designates the end 98 of part 22 as well as threaded portion 104. Although the velocity of part 22 moving through test section 18 is variable, if its length is known in advance or can be calculated, the axis of curve 96 can be adjusted to display displacement or length as opposed to time which would be velocity sensitive. Since the series of angularly displaced radial measuring detectors generates profiles of the part 22, a plurality of groups of curves similar to 196 and 197 are generated simultaneously. By having more than one plurality of sets of curves, damage to threads in various locations circumferentially about a bolt or fastener can be monitored and detected. Furthermore, through examining differences in the outputs, variations in geometry in radial position on the workpiece can be evaluated. In addition, rotationally symmetric features can be evaluated since it can be assumed that one of the pair of radial detectors 176a, 176b; 178a, 178b; 180a, 180b; or 182a, 182b were to detect the feature.

Computer 32 provides powerful data evaluations and storage capabilities. Through evaluating a series of parts, various spatial form criteria can be developed. As shown in FIG. 7, various segments of bolt 22 can be created, for example lines 116 and 118 define a threaded portion 104, whereas lines 120 and 122 define a profile section of the bolt. Software can also enable the profile to be displayed in a desired part direction even when the parts are not loaded in one direction only (e.g. head first), and compiled data are stored on floppy disk media.

In addition to evaluating various dimensional configuration features of parts 22, inspection system 10 further includes magnetometer 114 which does not form a part of this invention but is shown to demonstrate that other features or workpieces can be evaluated along the spatial form features. Magnetometer 114 enables hardness and internal structural features of the part to be evaluated.

While the above description constitutes the preferred embodiments of the present invention, it will be appreciated that the invention is susceptible of modification, variation and change without departing from the proper scope and fair meaning of the accompanying claims.

I claim:

1. An inspection system for evaluating workpieces for conformance to configuration criteria, comprising:

track means for causing said workpieces to translate through a test section said track means including a slit in said test section, said test section including a light source for producing a sheet of light having a width greater than its thickness, said light source oriented with respect to said track means such that said sheet of light passes through said slit without being occluded by said track means and said workpieces pass through said sheet of light upon passing through said test section, said sheet of light oriented such that said width is perpendicular to the direction of translation of said workpieces through said test section, said test section further having a first and second photodetector constructed and arranged side-by-side which in combination receive said sheet of light wherein the portion of the sheet of light received by each of said first and second photodetectors is partially occluded and provides a first and second single channel output signal each related to the intensity of said sheet of light incident on each of said photodetectors whereby said intensity is related to the degree to which said sheet of light is occluded by said workpieces over said respective adjacent first and second photodetectors as said workpieces translate through said test section, and signal processing means for receiving said first and second single channel photodetector output signals and for producing a value related to the section thickness of said workpieces as measured perpendicular to the direction of said translation.

2. An inspection system according to claim 1 wherein each of said photodetector single channel outputs is an analog signal related to said degree of occlusion of said first and second photodetectors, respectively, and wherein by combining said respective outputs, a degree of total occlusion for said workpiece can be determined.

3. An inspection system according to claim 1 wherein said sheet of light width is greater than said section thickness.

4. An inspection system according to claim 1 further comprising a plurality of said light sources oriented at angularly displaced positions and having a plurality of pairs of said photodetectors associated with said plurality of light sources whereby asymmetry of said workpieces produces different ratios of output signals from respective adjacent pairs of first and second photodetectors for said plurality of pairs of said photodetectors.

5. An inspection system according to claim 1 wherein said first and second photodetectors are oriented along a line.

6. An inspection system according to claim 1 wherein one of said photodetectors is operable to receive light occluded from one side profile of the part substantially from the center line of the part to the one side profile, and the other of said photodetectors is operable to receive light occluded from the other side profile of the part opposite the center line of the one side profile substantially from the center line of the part to the other side profile.

7. An inspection system according to claim 1 further comprising a beam splitter optically disposed between said light source and said first and second photodetectors operable to pass the sheet of light to said first and second photodetectors, and operable to reflect a substantially equal portion comprising a reflected sheet of light wherein said sheet of light and said reflected sheet of light in combination comprise the light generated by said light source; and, third and fourth photodetectors constructed and arranged side-by-side in contact with each other at approximately the center line of a part to be inspected for receiving the reflected light from said light source;

wherein light which impinges on said third and fourth photodetectors is detected and subtracted from partially occluded light from first and second photodetectors which cancels out any light source noise or scintillation.

8. An inspection system for evaluating workpieces for conformance to configuration criteria, comprising:

track means for causing said workpieces to translate through a test section said track means including a slit in said test section, said test section including a first light source for producing a first sheet of light having a greater than its thickness, said first light source oriented with respect to said track means such that said workpieces pass through first said sheet of light upon passing through said test section, said first sheet of light oriented such that said length is parallel to the direction of translation of said workpieces through said test section, said test section further having a first photodetector for receiving said first sheet of light and providing an output signal related to the intensity of said first sheet of light incident on said first photodetector, whereby said intensity is related to the degree to which said first sheet of light is occluded by said workpieces as said workpieces translate through said test section, said test section including a second light source for producing a second sheet of light having a length greater than its thickness, said second light source oriented with respect to said track means such that said sheet of light passes through said slit without being occluded by said track means and said workpieces pass through said second sheet of light upon passing through said test section, said second sheet of light oriented such that said length is perpendicular to the direction of translation of said workpieces through said test section, said test section further having a second and third photodetector for receiving said second sheet of light and providing an output signal related to the intensity of said second sheet of light incident on said second and third photodetectors, respectively, whereby said intensity is related to the degree to which said second sheet of light is occluded by said workpieces as said workpieces translate through said test section, and signal processing means for receiving said first, second, and third photodetector output signals and for producing values related to the length of said workpieces as measured in the direction of said translation and the cross-sectional configuration of said workpieces as measured perpendicular to said direction of translation.

9. An inspection system according to claim 8 wherein said track means is inclined whereby said workpieces are translated through said test section under the influence of gravity.

10. An inspection system according to claim 8 wherein said sheet of light is comprised of parallel rays whereby said sheet of light width and thickness do not vary appreciably upon passing through said test section.

11. An inspection system according to claim 8 wherein said first photodetector provides a single channel output which is an analog signal related to said degree of occlusion.

12. An inspection system according to claim 8 wherein said second and third photodetectors each provide a single channel output which is an analog signal and wherein said pair of analog signals are in combination related to said degree of occlusion.

13. An inspection system according to claim 8 wherein said first sheet of light thickness is less than the width of said workpieces measured perpendicular to said direction of translation.

14. An inspection system according to claim 8 wherein said second sheet of light thickness is less than the length of said workpieces measured parallel to said direction of translation.

15. An inspection system according to claim 8 wherein said second sheet of light width is greater than the width of said workpieces measured perpendicular to said direction of translation.

16. An inspection system according to claim 8 further comprising at least one third light source for generating a point of light and a point photodetector for receiving said point of light within said test section displaced from said first sheet of light along said direction of translation whereby the length of said workpieces as measured parallel to said direction of translation can be evaluated by output signals from said point photodetector and said first photodetector thereby enabling workpieces having a length which exceeds the width of said sheet of light to be evaluated.

17. An inspection system according to claim 8 further comprising a plurality of said second light sources oriented at angularly displaced positions and having a plurality of said pairs of said second and third photodetectors associated with said plurality of said second light sources whereby asymmetry of said workpieces produces different ratios of output signals from each of said plurality of said pairs of second and third photodetectors.

18. An inspection system according to claim 17 wherein each of said second light sources is alternately turned on individually, so as to alternate modulation of said second light sources which prevents photodetection by said second and third photodetectors of non-associated ones of said light sources.

* * * * *